United States Patent [19]

Kurmeier et al.

[11] Patent Number: 5,292,454
[45] Date of Patent: Mar. 8, 1994

[54] TRIFLUOROTOLUENE COMPOUNDS, AND A LIQUID CRYSTALLINE MEDIUM

[75] Inventors: Hans A. Kurmeier, Seeheim-Jugenheim; Reinhard Hittich, Modautal; Eike Poetsch, Mühltal; Volker Meyer, Gross-Zimmern; Herbert Plach, Darmstadt; David Coates, Merley Wimborne, all of Fed. Rep. of Germany

[73] Assignee: Merck Patent Gesellschaft mit beschränkter Haftung, Darmstadt, Fed. Rep. of Germany

[21] Appl. No.: 865,727

[22] Filed: Apr. 9, 1992

Related U.S. Application Data

[63] Continuation of Ser. No. 549,000, Jul. 26, 1990, abandoned.

[30] Foreign Application Priority Data

May 26, 1989 [DE] Fed. Rep. of Germany ....... 3917119

[51] Int. Cl.$^5$ ..................... C09K 19/12; C09K 19/30; G02F 1/13
[52] U.S. Cl. .............. 252/299.66; 252/299.63; 359/103
[58] Field of Search .................. 252/299.66, 299.63

[56] References Cited

U.S. PATENT DOCUMENTS

| | | | |
|---|---|---|---|
| 4,330,426 | 5/1982 | Eidenschink et al. | 252/299.63 |
| 4,505,837 | 3/1985 | Romer et al. | 252/299.66 |
| 4,871,469 | 10/1989 | Reiffenrath et al. | 252/299.61 |

FOREIGN PATENT DOCUMENTS 0256636 2/1988 European Pat. Off. .

Primary Examiner—Robert L. Stoll
Assistant Examiner—C. Harris
Attorney, Agent, or Firm—Millen, White, Zelano, & Branigan

[57] ABSTRACT

Trifluorotoluene compounds of the formula I

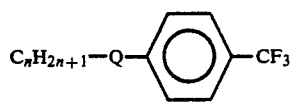

in which n is 1 to 12, and Q is

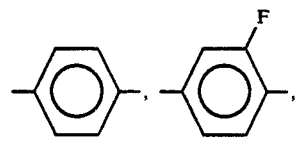

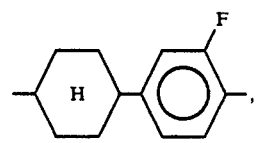

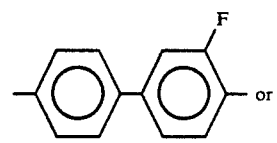

or

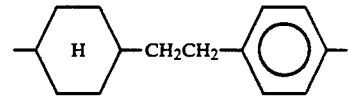

are suitable as components of liquid-crystalline media.

6 Claims, No Drawings

TRIFLUOROTOLUENE COMPOUNDS, AND A LIQUID CRYSTALLINE MEDIUM

This application is a continuation of application Ser. No. 07/549,000, filed Jul. 26, 1990, abandoned.

The invention relates to trifluorotoluene compounds of the formula I

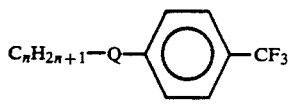   I in which n is 1 to 12, and Q is

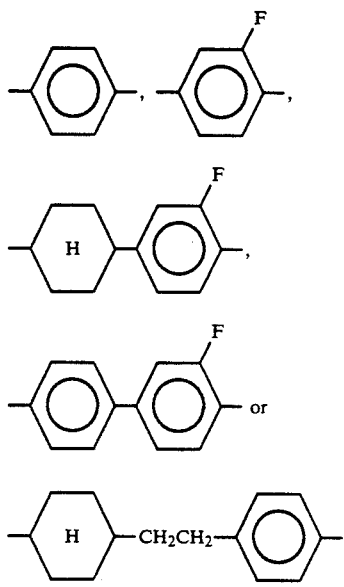

The invention furthermore relates to the use of these compounds as components of liquid-crystalline media, and to liquid-crystal and electrooptical display elements which contain the liquid-crystalline media according to the invention.

The compounds of the formula I can be used as components of liquid-crystalline media, in particular for displays based on the principle of the twisted cell, including highly twisted cells, the guest/host effect, the effect of deformation of aligned phases or the effect of dynamic scattering.

The invention had the object of finding novel, stable liquid-crystalline or mesogenic compounds which are suitable as components of liquid-crystalline media and, in particular, simultaneously have relatively low viscosity and relatively high dielectric anisotropy.

It has now been found that compounds of the formula I are preeminently suitable as components of liquid-crystalline media. In particular, they have comparatively low viscosities. Using them, stable liquid-crystalline media having a broad mesophase range, very good low-temperature behaviour, very high electrical resistance and advantageous values for the optical and dielectric anisotropy can be obtained.

Derivatives 4'-hydroxy-4-trifluoromethylbiphenyl which have liquid-crystalline properties have already been disclosed (P. Le Barny et al., Mol. Cryst. Liq. Cryst., 1985, Vol. 127, pp. 413–429). However, these compounds have a highly smectogenic character and are less suitable for many practical applications.

Recently, 4-(2-(4-trans-alkylcyclohexyl)phenyl)ethyl)-p-benzotrifluorides (J. C. Liong et al., Mol. Cryst. Liq. Cyrst. 1989, Vol. 167, pp. 253–258) have been described. These compounds are either isotropic or have relatively highly ordered smectic ($S_+$) phases, which appears to make them unsuitable for practical applications.

In addition, the provision of the compounds of the formula I very generally considerably broadens the range of liquid-crystalline substances which are suitable, from various applicational points of view, for the preparation of liquid-crystalline mixtures.

The compounds of the formula I have a broad field of application. Depending on the choice of the substituents, these compounds can be used as base materials from which liquid-crystalline media are predominantly composed; however, it is also possible to add compounds of the formula I to liquid-crystalline base materials from other classes of compound, in order, for example, to affect the dielectric and/or optical anisotropy of a dielectric of this type and/or to optimize its threshold voltage and/or its viscosity.

In the pure state, the compounds of the formula I are colourless and form liquid-crystalline mesophases in a temperature range which is favourable for electrooptical use. They are stable chemically, thermally and to light.

The invention thus relates to the compounds of the formula I, and to the use of these compounds as components of liquid-crystalline media. The invention furthermore relates to liquid-crystalline media containing at least one compound of the formula I, and to liquid-crystal display elements, in particular electrooptical display elements, which contain media of this type.

Accordingly, the compounds of the formula I cover compounds of the sub-formulae Ia–Ie:

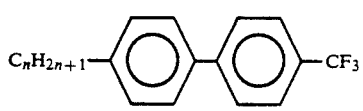   Ia

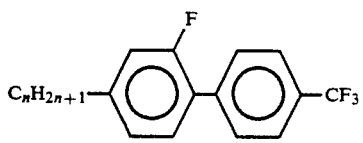   Ib

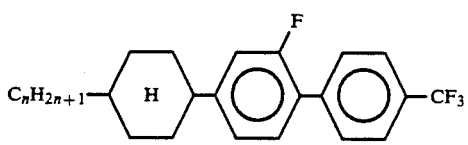   Ic

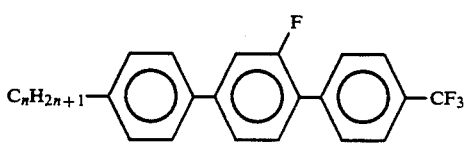   Id

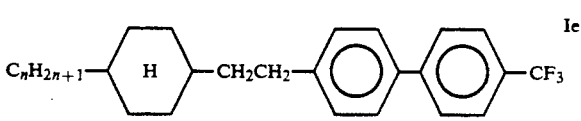   Ie

Ia, Ib and Ic, but in particular Ic, are particularly preferred.

The radical $C_nH_{2n+1}$ may be straight-chain or branched. It is preferably straight-chain, has 2, 3, 4, 5, 6 or 7 C atoms and accordingly is preferably ethyl, propyl, butyl, pentyl, hexyl, heptyl, furthermore methyl, octyl, nonyl, decyl, undecyl or dodecyl.

Compounds of the formula I containing branched radicals $C_nH_{2n+1}$ may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl and 2-propylpentyl.

The formula I covers racemates of these compounds and the optical antipodes, and mixtures thereof.

Of these compounds of the formula I and the subformulae, those are preferred in which at least one of the radicals present therein has one of the preferred meanings given.

The compounds of the formula I are prepared by methods known per se, as described in the literature (for example in the standard works, such as Houben-Weyl, Methoden der Organischen Chemie, Georg-Thieme-Verlag, Stuttgart, Vol. IX, pp. 867 ff.), to be precise under reaction conditions which are known and suitable for the reactions mentioned. Use may also be made here of variants which are known per se, but are not described here in greater detail.

The compounds of the formula I according to the invention are preferably prepared by coupling appropriate zinc organyls with p-bromotrifluorotoluene with transition-metal catalysis. The process conditions, which are known per se, are given in WO 88/02357 and in the article by E. Poetsch, Kontakte (Darmstadt) 1988 (2), pp. 15-28.

The compounds of the formula I according to the invention are furthermore preferably prepared by reacting the benzoic acids conforming to the formula I with dialkylaminosulfur trifluorides, for example DAST (diethylaminosulfur trifluoride) [W. J. Middleton, J. Org. Chem. 40 (1975), 547] or sulfur tetrafluoride [A. Haus, M. Spitzer, M. Lieb, Chem. Ber. 121 (1988) 1329], in accordance with the equation

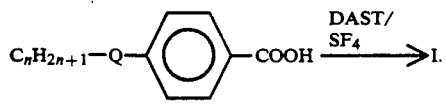

The benzoic acids conforming to the formula I can be prepared, for example, by hydrolysis of the carbonitriles conforming to the formula I.

If desired, starting materials may also be formed in situ by not isolating them from the reaction mixture, but instead immediately reacting them further to form the compounds of the formula I.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further components are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a divalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are also common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also contain components from the group comprising the compounds 1b, 2b, 3b, 4b and 5b (Group 2), whose proportions are preferably as follows: Group 1: 20 to 90%, in particular 30 to 90%, Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The examples below are intended to illustrate the invention without representing a limitation. Above and below, percentages are per cent by weight. All temperatures are indicated in degrees Celsius. M.p. means melting point, C.p.=clear point. Furthermore, C=crystalline state, N=nematic phase, S=smectic phase and I=isotropic phase. The numbers between these symbols represent the transition temperatures. $\Delta$n indicates optical anisotropy (589 nm, 20° C.), and the viscosity (mm$^2$/sec) was determined at 20° C.

"Customary work-up" means: water is added if appropriate, the mixture is extracted with methylene chloride, diethyl ether or toluene, the organic phase is separated off, dried and evaporated, and the product is purified by distillation and/or chromatography. The following abbreviations are used:

DAST: Diethylaminosulfur trifluoride
DCC: Dicyclohexylcarbodiimide
DDQ: Dichlorodicyanobenzoquinone
DIBALH: Diisobutylaluminium hydride
POT: Potassium tertiary-butanolate
THF: Tetrahydrofuran
pTSOH: p-Toluenesulfonic acid

EXAMPLE 1

11.2 g of anhydrous zinc bromide in 25 ml of THF are added dropwise at about 0° to a Grignard solution prepared from 20 g of 4-n-propylbromobenzene and 2.4 g of magnesium turnings in 100 ml of THF. After the mixture has been stirred for 2 hours, a mixture of 22.5 g of 4-bromotrifluorotoluene, 1.5 g of [(diphenylphosphine)ferrocenyl]palladium(II) chloride and 25 ml of THF is added dropwise, and the mixture is stirred for 24 hours at room temperature and poured into 100 ml of saturated ammonium chloride solution. Customary work-up gives 4-(4-n-propylphenyl)trifluorotoluene, M.p. 97° C., $\Delta\epsilon$=14.2, viscosity $\eta$ (20° C.)=6 mm$^2$/s.

EXAMPLE 2

An anhydrous solution of 60.0 g of sodium trifluoroacetate in 350 ml of 1-methyl-2-pyrrolidone is added under nitrogen at 160° C. over the course of 4 hours to an anhydrous, vigorously stirred mixture of 40.3 g of 4'-(4-trans-pentylcyclohexyl)-2'-fluoro-4-bromobiphenyl, 38.0 g of copper(I) iodide and 300 ml of 1-methyl-2-pyrrolidone which additionally contains 0.33 mol of cis-, trans-trans-1,5,9-cyclododecatriene (as carbene scavenger). The reaction mixture is subsequently stirred at 160° C. for a further 3.5 hours. After cooling, the NMP is removed by vacuum distillation. The evaporation residue, still warm at about 80° C., is stirred with 500 ml of toluene and 400 ml of saturated sodium chloride solution. The copper salts are filtered off with suction and washed with toluene, and the organic phase of the filtrate is separated off, washed with sodium chloride solution, dried over sodium sulphate and evaporated in vacuo. The evaporation residue is dissolved in dichloromethane, adsorbed onto silica gel and purified by column chromatography (silica gel/petroleum ether 40°-80°). Recrystallization from isopropyl alcohol gives 4-(2-fluoro-4-(trans-4-pentylcyclohexyl)phenyl)trifluorotoluene;C78.7 N (74.2), $\Delta\epsilon$=14.9, $\eta$ (20° C.)=37 mm$^2$/s

EXAMPLES 3 to 40

The following compounds are prepared analogously to Example 1:

(3) 4-(4-methylphenyl)trifluorotoluene
(4) 4-(4-ethylphenyl)trifluorotoluene
(5) 4-(4-n-butylphenyl)trifluorotoluene
(6) 4-(4-n-pentylphenyl)trifluorotoluene
(7) 4-(4-n-hexylphenyl)trifluorotoluene
(8) 4-(4-n-heptylphenyl)trifluorotoluene
(9) 4-(4-n-octylphenyl)trifluorotoluene
(10) 4-(4-n-nonylphenyl)trifluorotoluene
(11) 4-(4-n-decylphenyl)trifluorotoluene
(12) 4-(4-n-undecylphenyl)trifluorotoluene
(13) 4-(4-n-dodecylphenyl)trifluorotoluene
(14) 4-(2-fluoro-4-methylphenyl)trifluorotoluene
(15) 4-(2-fluoro-4-ethylphenyl)trifluorotoluene
(16) 4-(2-fluoro-4-n-propylphenyl)trifluorotoluene
(17) 4-(2-fluoro-4-n-butylphenyl)trifluorotoluene
(18) 4-(2-fluoro-4-n-pentylphenyl)trifluorotoluene
m.p. 59° C., $\Delta\epsilon$=16.1, $\eta$ (20° C.)=7 mm$^2$/s

(19) 4-(2-fluoro-4-n-hexylphenyl)trifluorotoluene
(20) 4-(2-fluoro-4-n-heptylphenyl)trifluorotoluene
(21) 4-(2-fluoro-4-n-octylphenyl)trifluorotoluene
(22) 4-(2-fluoro-4-n-nonylphenyl)-trifluorotoluene
(23) 4-(2-fluoro-4-n-decylphenyl)-trifluorotoluene
(24) 4-(2-fluoro-4-n-undecylphenyl)trifluorotoluene
(25) 4-(2-fluoro-4-n-dodecylphenyl)trifluorotoluene
(26) 4-(2-fluoro-4-(trans-4-methylcyclohexyl)-phenyl)trifluorotoluene
(27) 4-(2-fluoro-4-(trans-4-ethylcyclohexyl)-phenyl)-trifluorotoluene
(28) 4-(2-fluoro-4-(trans-4-n-propylcyclohexyl)-phenyl)trifluorotoluene
(29) 4-(2-fluoro-4-(trans-4-n-butylcyclohexyl)-phenyl)trifluorotoluene
(30) 4-(2-fluoro-4-(trans-4-n-hexylcyclohexyl)-phenyl)trifluorotoluene
(31) 4-(2-fluoro-4-(trans-4-n-heptylcyclohexyl)-phenyl)trifluorotoluene
(32) 4-(2-fluoro-4-(trans-4-n-octylcyclohexyl)-phenyl)trifluorotoluene
(33) 4-(2-fluoro-4-(trans-4-n-nonylcyclohexyl)-phenyl)trifluorotoluene
(34) 4-(2-fluoro-4-(trans-4-n-decylcyclohexyl)-phenyl)trifluorotoluene
(35) 4-(2-fluoro-4-(trans-4-n-undecylcyclohexyl)-phenyl)trifluorotoluene
(36) 4-(2-fluoro-4-(trans-4-n-dodecylcyclohexyl)-phenyl)trifluorotoluene
(37) 4-(4'-propylbiphenyl-3-fluoro-4-yl)trifluorotoluene
(38) 4-(4'-pentylbiphenyl-3-fluoro-4-yl)trifluorotoluene
(39) 4-[p-trans-4-propylcyclohexyl)-ethyl-phenyl]trifluorotoluene
(40) 4-[p-(trans-4-pentylcyclohexyl)-ethyl-phenyl]trifluorotoluene

We claim:
1. A nematic liquid-crystalline medium having at least two liquid-crystalline components, which contains at least one trifluorotoluene compound of the formula I

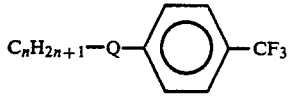   I in which n is 1 to 12, and Q is

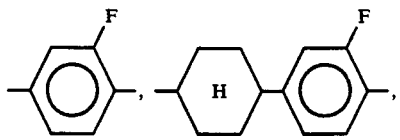

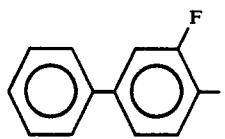

2. A medium according to claim 1, wherein $C_nH_{2n+1}$ is a straight-chain alkyl radical of 2 to 7 C atoms.

3. An electrooptical display element based on the principle of the twisted cell, which contains a nematic liquid-crystalline medium according to claim 1.

4. A nematic liquid-crystalline medium having at least two liquid-crystalline components, which contains at least one trifluorotoluene compound of the formula

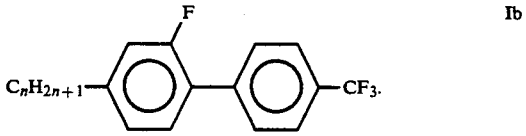   Ib wherein n is 1 to 12.

5. A nematic liquid-crystalline medium having at least two liquid-crystalline components, which contains at least one trifluorotoluene compound of the formula

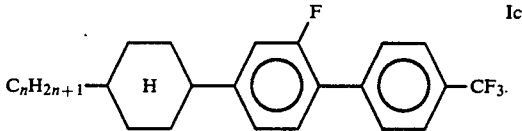   Ic wherein n is 1 to 12.

6. A nematic liquid-crystalline medium having at least two liquid-crystalline components, which contains at least one trifluorotoluene compound of the formula

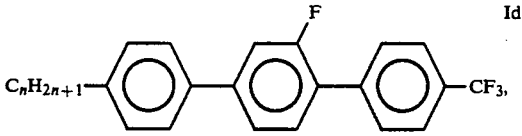   Id wherein n is 1 to 12.

* * * * *